US012797565B2

(12) United States Patent
Konishi et al.

(10) Patent No.: US 12,797,565 B2
(45) Date of Patent: Nov. 17, 2026

(54) CPAP DEVICE

(71) Applicant: Murata Manufacturing Co., Ltd., Kyoto (JP)

(72) Inventors: Yoshiro Konishi, Kyoto (JP); Keisuke Inaba, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 534 days.

(21) Appl. No.: 18/474,550

(22) Filed: Sep. 26, 2023

(65) Prior Publication Data

US 2024/0115821 A1 Apr. 11, 2024

(30) Foreign Application Priority Data

Oct. 6, 2022 (JP) ................................ 2022-161643

(51) Int. Cl.
*A61M 16/00* (2006.01)
*A61M 16/10* (2006.01)
*A61M 16/16* (2006.01)

(52) U.S. Cl.
CPC ........ *A61M 16/0066* (2013.01); *A61M 16/16* (2013.01); *A61M 16/107* (2014.02)

(58) Field of Classification Search
CPC ..... A61M 16/0057–0069; A61M 16/021–022; A61M 16/08; A61M 16/0816; A61M 16/0875–0883; A61M 16/105–106; A61M 16/107–1095; A61M 16/14; A61M 16/16–168; A61M 2205/3626
See application file for complete search history.

(56) References Cited

U.S. PATENT DOCUMENTS

| | | | | |
|---|---|---|---|---|
| 2020/0330720 | A1* | 10/2020 | Formica .............. | A61M 16/109 |
| 2022/0016377 | A1 | 1/2022 | Maeda et al. | |
| 2023/0060994 | A1* | 3/2023 | Austin .............. | A61M 16/0003 |
| 2023/0144677 | A1* | 5/2023 | McMahon ............ | A61M 16/06 128/204.23 |
| 2023/0381444 | A1* | 11/2023 | Yu ..................... | A61M 16/0066 |

FOREIGN PATENT DOCUMENTS

| | | | |
|---|---|---|---|
| WO | 2020/217843 | A1 | 10/2020 |
| WO | 2021/010027 | A1 | 1/2021 |

* cited by examiner

*Primary Examiner* — Rachel T Sippel
(74) *Attorney, Agent, or Firm* — McDonald Hopkins LLC

(57) ABSTRACT

A CPAP device includes a main unit including a first electric circuit including a blower and a connection terminal connected to the first electric circuit, and a base unit connectable to the main unit, including a blower tube, a second electric circuit different from the first electric circuit, and a connection terminal connected to the second electric circuit. The main unit has a first electrical connection portion including an exposed portion of the connection terminal and a first peripheral portion surrounding the first electrical connection portion. The base unit has a second electrical connection portion including an exposed portion of the connection terminal and a second peripheral portion surrounding the second electrical connection portion.

8 Claims, 13 Drawing Sheets

CPAP DEVICE

CROSS REFERENCE TO RELATED APPLICATION

This application claims priority from Japanese Patent Application No. 2022-161643 filed on Oct. 6, 2022. The content of this application is incorporated herein by reference in its entirety.

BACKGROUND OF THE DISCLOSURE

1. Field of the Disclosure

The present disclosure relates to a CPAP device including a main unit and a base unit.

2. Description of the Related Art

International Publication No. 2020/217843 describes a CPAP device including a main body unit (main unit) and a base unit. The main body unit may be used alone, but may be used in combination with the base unit.

When the main body unit and the base unit are used in combination, the main body unit is attached and fixed to the base unit. In the case above, the main body unit and the base unit each have an electrical contact (connection terminal) exposed from the housing. The main body unit and the base unit are electrically connected to each other by bringing the electrical contacts into contact with each other.

The CPAP device also includes a container for storing water in the base unit. The CPAP device heats and vaporizes water in the container and supplies the vaporized water to a user together with a blown gas.

However, in the configuration of the CPAP device in the related art, when water is supplied to the container or in use, the water may reach the electrical contacts and cause undesired short circuit such as short circuit between multiple connection terminals, for example.

BRIEF SUMMARY OF THE DISCLOSURE

Therefore, it is a possible benefit of the present disclosure to provide a CPAP device capable of suppressing an undesired short circuit.

A CPAP device of the present disclosure includes a main unit including a first electric circuit including a blower and a first connection terminal connected to the first electric circuit, and a base unit connectable to the main unit, including a blower tube, a second electric circuit, and a second connection terminal connected to the second electric circuit.

The main unit includes a first electrical connection portion including an exposed portion of the first connection terminal and a first peripheral portion surrounding the first electrical connection portion. The base unit includes a second electrical connection portion including an exposed portion of the second connection terminal and a second peripheral portion surrounding the second electrical connection portion. A first distance with which the first peripheral portion and the second peripheral portion face each other has a portion shorter than a second distance with which a proximal portion of the first electrical connection portion around the first connection terminal and a proximal portion of the second electrical connection portion around the second connection terminal face each other.

In the configuration described above, water from the outside of the first peripheral portion and the second peripheral portion is held between the first peripheral portion and the second peripheral portion, and does not enter between the first electrical connection portion and the second electrical connection portion.

According to the present disclosure, an undesired short circuit may be suppressed.

DETAILED DESCRIPTION OF THE DISCLOSURE

A CPAP device according to an embodiment of the present disclosure will be described with reference to the drawings.

CPAP Device 10 Overview

Figure 1:
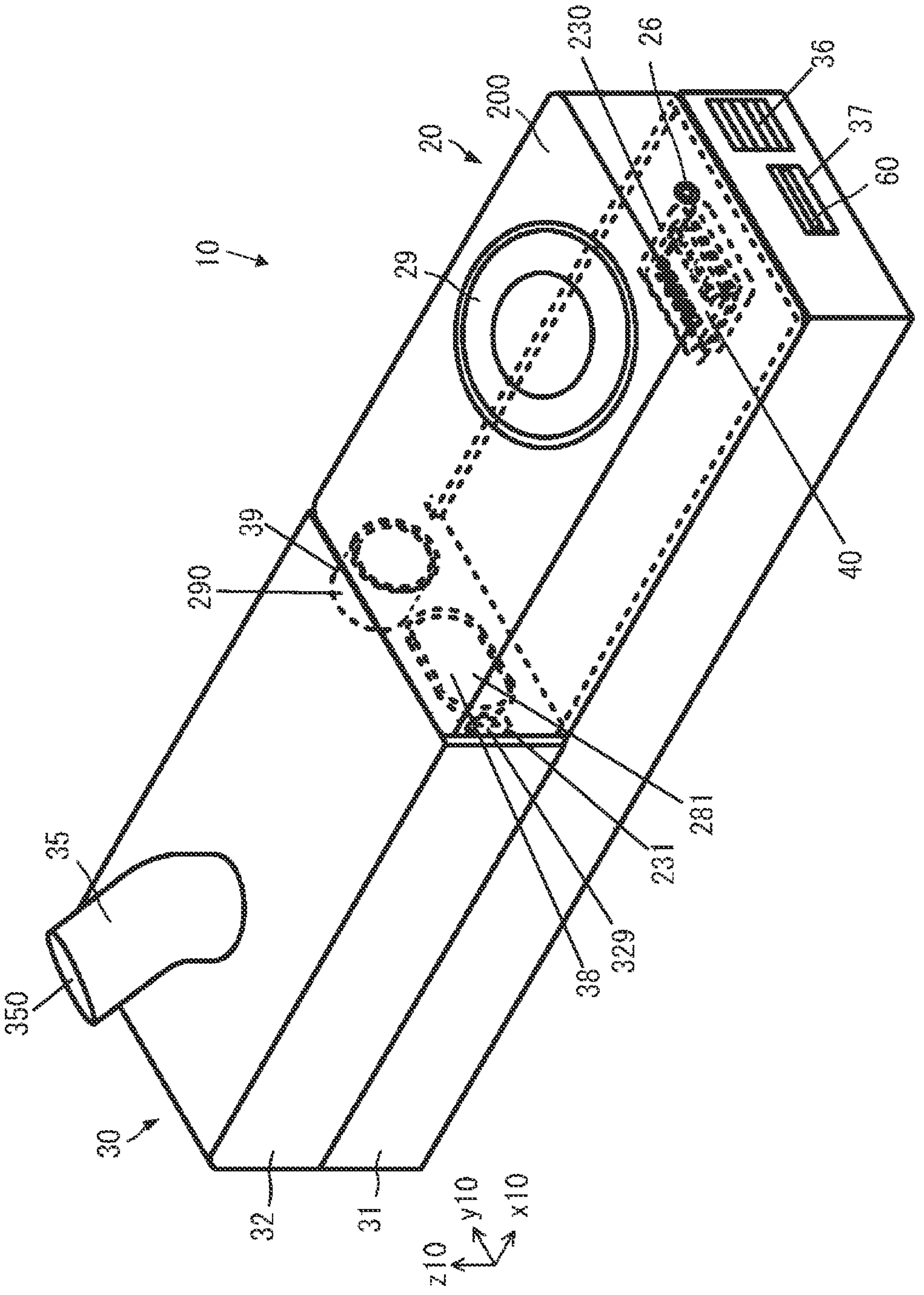
FIG. 1 is an external perspective view of a CPAP device according to an embodiment of the present disclosure.
Figure 2:
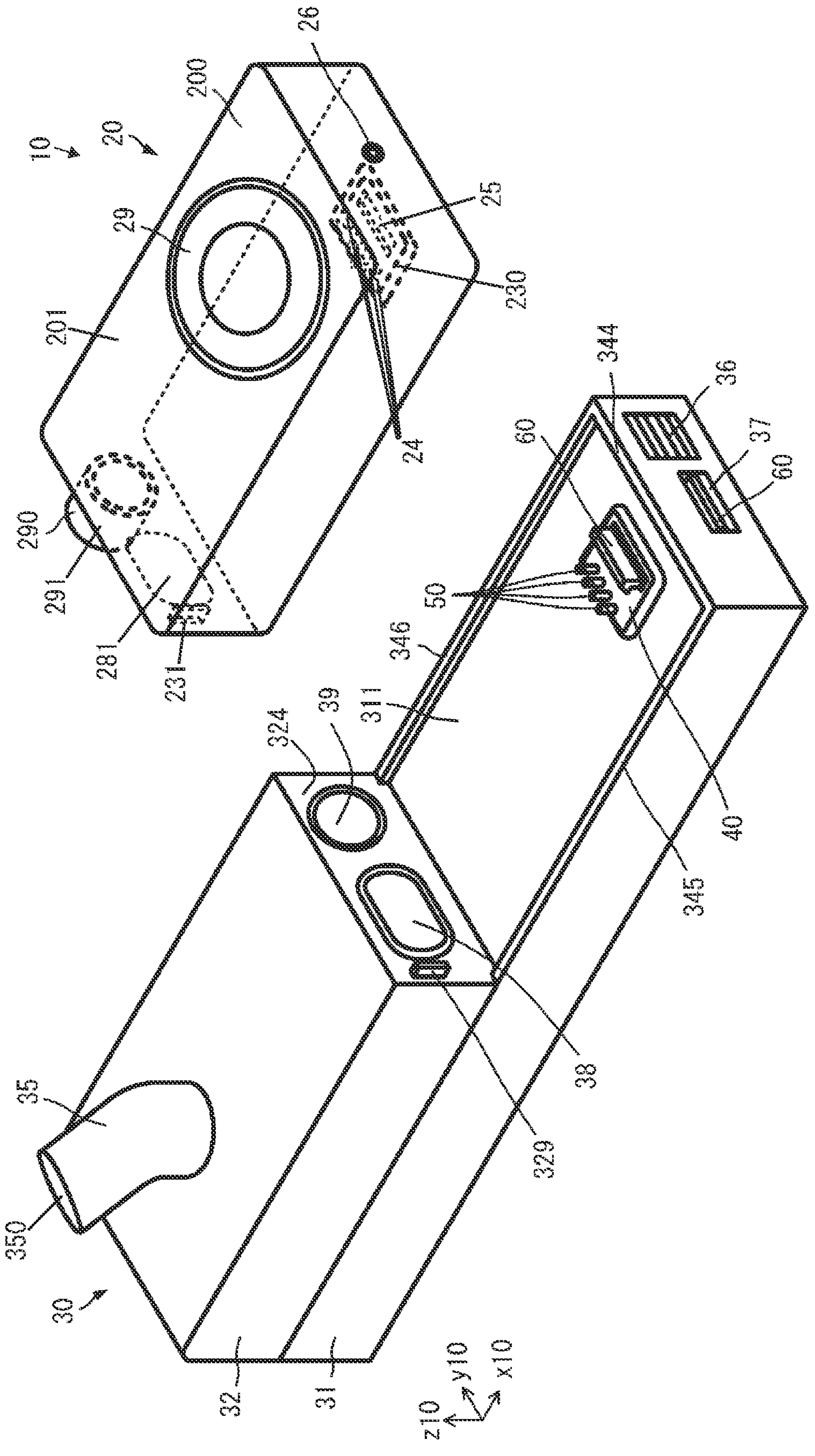
FIG. 2 is an external perspective view of the CPAP device according to the embodiment of the present disclosure.
Figure 3:
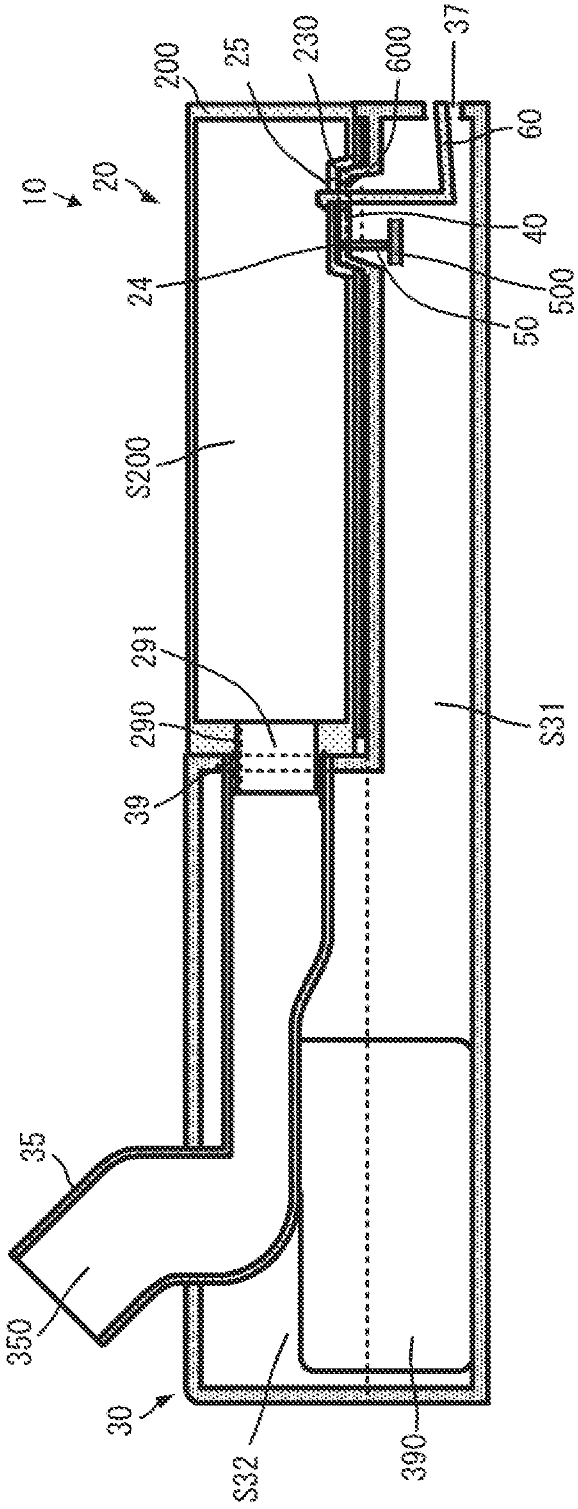
FIG. 3 is a side sectional view of the CPAP device according to the embodiment of the present disclosure.

FIG. 1 and FIG. 2 are each an external perspective view of the CPAP device according to the embodiment of the present disclosure. FIG. 3 is a side sectional view of the CPAP device according to the embodiment of the present disclosure. A state in which the main unit is attached to the base unit (state in which main unit and base unit are coupled to each other) is illustrated in FIG. 1 and FIG. 3, and a state in which the main unit is detached from the base unit is illustrated in FIG. 2.

A CPAP device 10 includes a main unit 20 and a base unit 30 as illustrated in FIG. 1, FIG. 2, and FIG. 3.

The main unit 20 has a rectangular shape having a long side direction and a short side direction in plan view. Note that the rectangular shape in the present embodiment is not limited to a perfect rectangular shape, and includes a shape with various chamfered corners. An outer shape of the main unit 20 is a rectangular parallelepiped, and a height is shorter than a length in the long side direction and a length in the short side direction. Note that the rectangular parallelepiped in the present embodiment is not limited to a perfect rectangular parallelepiped, and includes a rectangular parallelepiped having various chamfered apexes and edges.

The base unit 30 has a rectangular shape having a long side direction and a short side direction in plan view. The base unit 30 has a high height portion and a low height portion, and the high height portion is higher than the low height portion. That is, an outer shape of the base unit 30 is a shape in which a high height portion of a rectangular parallelepiped and a low height portion of a rectangular parallelepiped are connected in the long side direction of the base unit 30.

The main unit 20 may be attached to an upper surface of the low height portion of the base unit 30. In a state in which the main unit 20 is attached to the base unit 30, an outer shape of the CPAP device 10 is a rectangular parallelepiped.

In a state in which the main unit 20 is attached to the base unit 30 (attached state), a gas flow path of the main unit 20 and a gas flow path of the base unit 30 communicate with each other. Further, a first electric circuit of the main unit 20 and a second electric circuit of the base unit 30 are electrically connected to each other. Thus, the main unit 20 and the base unit 30 cooperate with each other to achieve a function of the CPAP device 10.

At this time, water is stored in the base unit 30, and in a state in which the main unit 20 is attached to the base unit 30, the CPAP device 10 supplies gas having predetermined humidity to a user by vaporizing the water.

In a state in which the main unit 20 is detached from the base unit 30, the main unit 20 alone operates to achieve the function of the CPAP device 10.

Specific contents of an attached state, a flow path, and an electrical connection of the main unit 20 and the base unit 30 will be described later, and a specific configuration example of the main unit 20 and the base unit 30 will be described first.

Main Unit 20

Figure 4A:
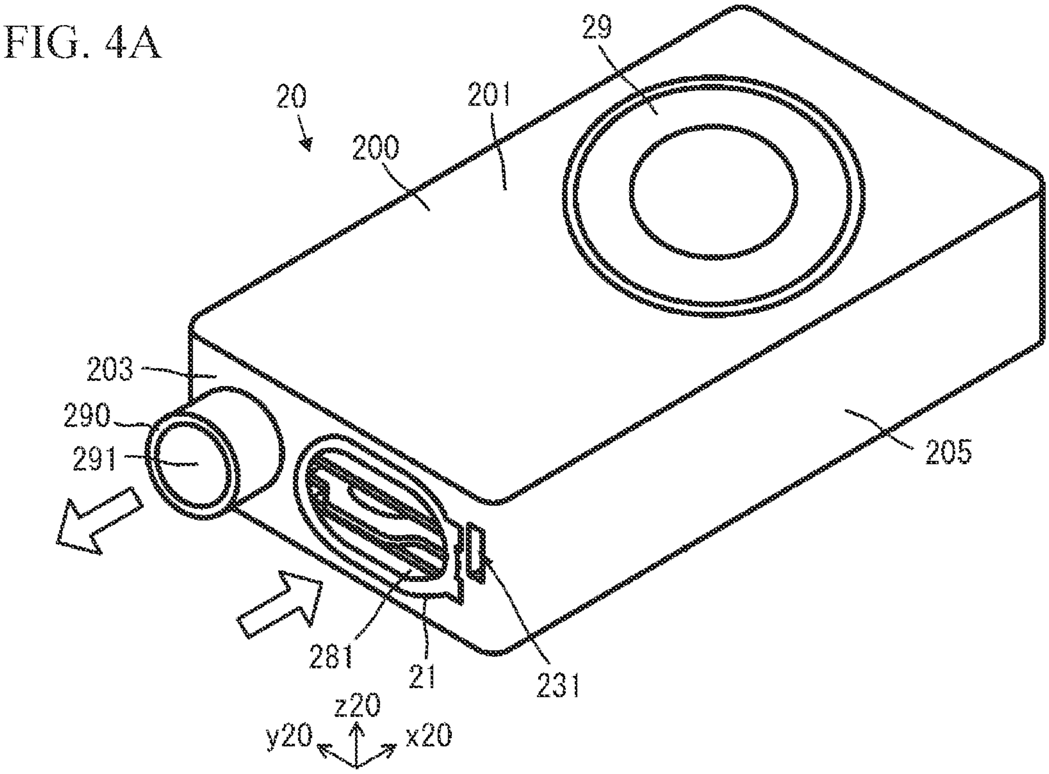
FIG. 4A and FIG. 4B are each an external perspective view of a main unit according to the embodiment of the present disclosure.
Figure 4B:
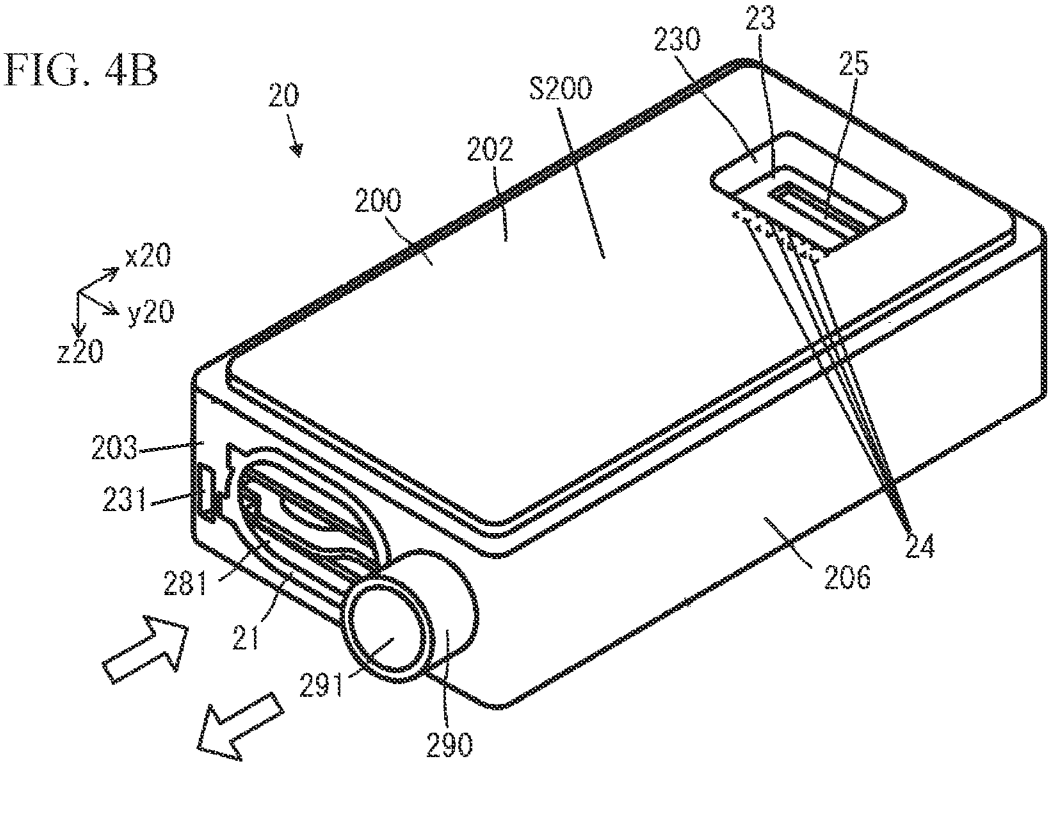
Figure 5A:
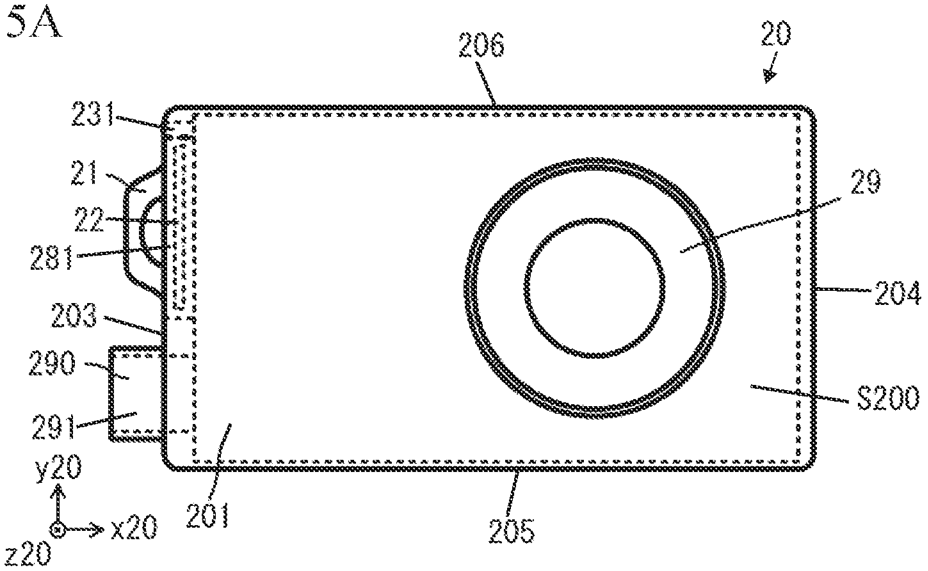
FIG. 5A is a top view of the main unit according to the embodiment of the present disclosure.
Figure 5B:
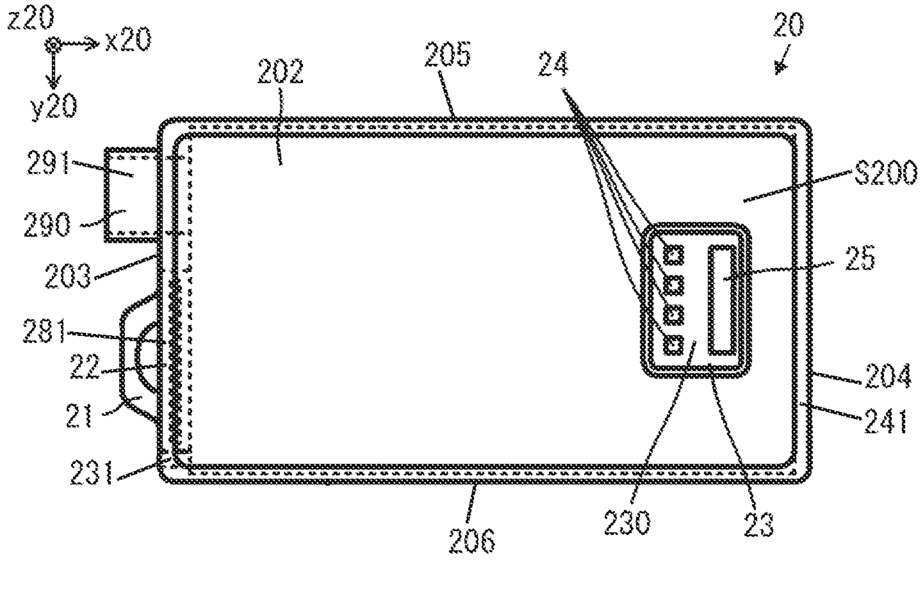
FIG. 5B is a bottom view of the main unit.
Figure 6A:
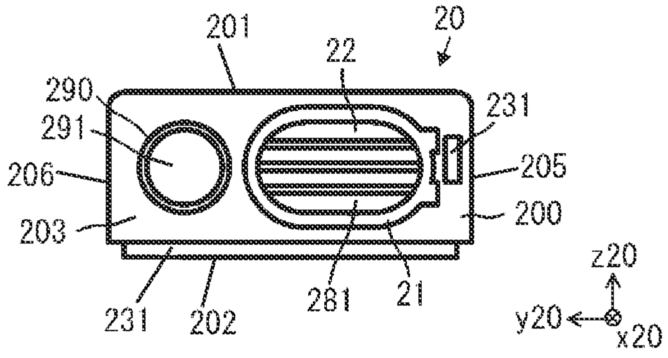
FIG. 6A, FIG. 6B, and FIG. 6C are each a side view of the main unit according to the embodiment of the present disclosure.
Figure 6B:
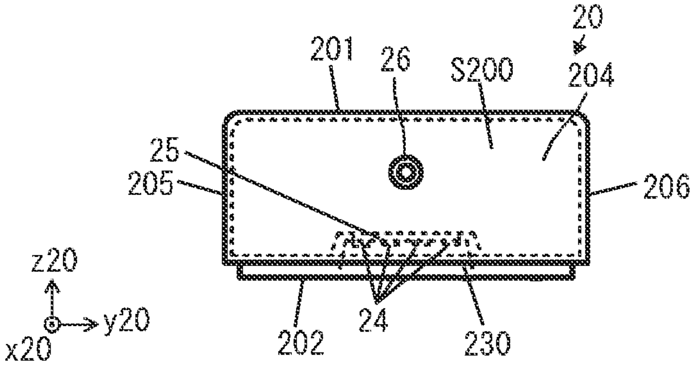
Figure 6C:
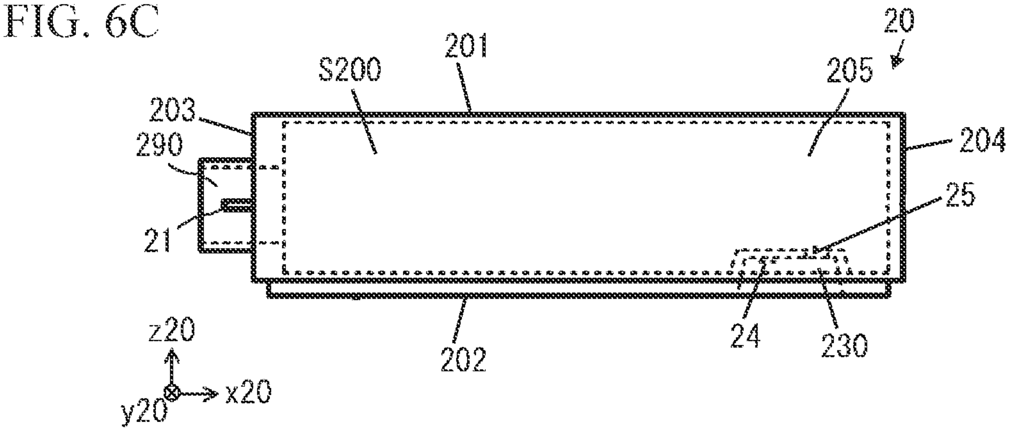
Figure 6D:
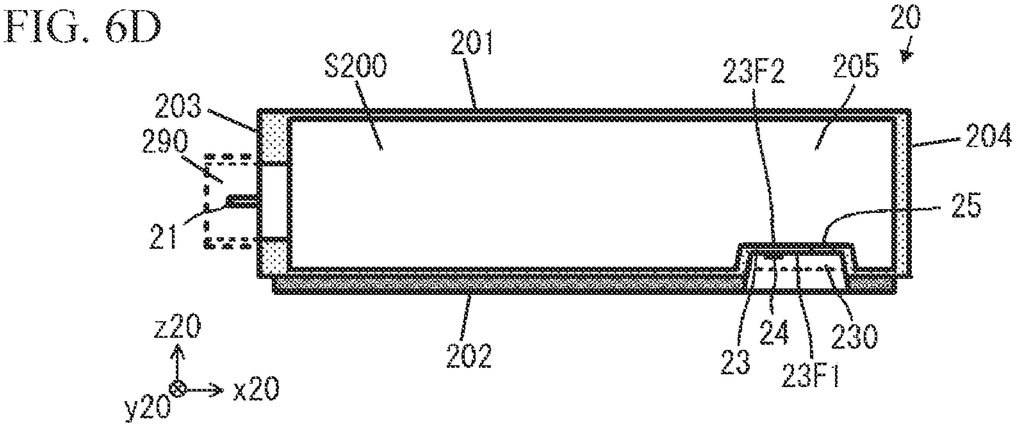
FIG. 6D is a side sectional view of the main unit according to the embodiment of the present disclosure.

FIG. 4A and FIG. 4B are each an external perspective view of the main unit according to the embodiment of the present disclosure. FIG. 4A is a view seen from an upper surface side, and FIG. 4B is a view seen from a lower surface side. FIG. 5A is a top view of the main unit according to the embodiment of the present disclosure, and FIG. 5B is a bottom view of the main unit. FIG. 6A, FIG. 6B, and FIG. 6C are each a side view of the main unit according to the embodiment of the present disclosure, and FIG. 6D is a side sectional view of the main unit according to the embodiment of the present disclosure. FIG. 6A is a view seen from a short side wall 203 side, FIG. 6B is a view seen from a short side wall 204 side, and FIG. 6C is a view seen from a long side wall 205 side. FIG. 6D is a side sectional view seen from the same side as in FIG. 6C.

The main unit 20 includes a housing 200 as illustrated in FIG. 4A, FIG. 4B, FIG. 5A, FIG. 5B, FIG. 6A, FIG. 6B, FIG. 6C, and FIG. 6D.

An outer shape of the housing 200 is a rectangular parallelepiped having a long side direction (x20-axis direction) and a short side direction (y20-axis direction), and having a predetermined height (length in z20-axis direction). The housing 200 has an upper wall 201, a lower wall 202, a side wall 203, a side wall 204, a side wall 205, and a side wall 206.

The upper wall 201 and the lower wall 202 are opposed to each other. The side wall 203 and the side wall 204 are side walls parallel to the short side direction and are opposed to each other. The side wall 205 and the side wall 206 are side walls parallel to the long side direction and are opposed to each other. The side wall 203, the side wall 204, the side wall 205, and the side wall 206 are each connected to peripheral portions of the upper wall 201 and the lower wall 202. Thus, the housing 200 has an inner space 5200 surrounded by the upper wall 201, the lower wall 202, the side wall 203, the side wall 204, the side wall 205, and the side wall 206. The first electric circuit is disposed in the inner space 5200 (specific illustration is omitted).

The side wall 203 has an inlet 281 and an outlet 291. The inlet 281 corresponds to a first inlet, and the outlet 291 corresponds to a first outlet. The inlet 281 and the outlet 291 each penetrate through the side wall 203 in a thickness direction. The inlet 281 and the outlet 291 allow the inner space 5200 of the housing 200 to communicate with an outer space of the housing 200. An outer surface of the side wall 203 corresponds to a flow path forming surface of the main unit 20.

The inlet 281 and the outlet 291 are disposed side by side in a width direction of the side wall 203. The inlet 281 and the outlet 291 are disposed in this order from one end portion to the other end portion in the width direction of the side wall 203. The one end portion in the width direction of the side wall 203 is an end portion at which the side wall 203 is connected to the side wall 205, and the other end portion is an end portion at which the side wall 203 is connected to the side wall 206.

A cylindrical body 290 is provided on the side wall 203. The cylindrical body 290 has a shape protruding from the outer surface of the side wall 203. The cavity in the center of the cylindrical body 290 is connected to the outlet 291 formed on the side wall 203, and this portion also functions as the outlet 291.

An air filter 22 is disposed in the inlet 281. A filter cover 21 is provided on an outer surface side of the air filter 22. The air filter 22 is fixed to the inlet 281 being sandwiched by the filter cover 21 and the side wall 203.

A recess 231 is formed in the side wall 203. The recess 231 is formed in the vicinity of one end portion of the side wall 203. That is, the recess 231 is disposed to be separated from the cylindrical body 290 forming the outlet 291 in the width direction of the side wall 203.

A power supply port 26 is disposed on the side wall 204. The power supply port 26 is connected to the first electric circuit in the inner space 5200. Electric power is supplied to the first electric circuit by connecting the power supply port 26 to an external power supply adapter.

An operation button 29 is disposed on the upper wall 201. The operation button 29 is connected to the first electric circuit in the inner space 5200. When the operation button 29 is operated, operations such as starting and stopping of the first electric circuit are controlled.

Specific Configuration of Recess 230 of Main Unit 20

A recess 230 is formed in the lower wall 202. The recess 230 has a shape recessed upward (toward the inside of the housing 200) from a surface (corresponding to a "second surface" of the present disclosure) of the lower wall 202. The recess 230 is formed at a position closer to the other end portion than to one end portion of the lower wall 202. The one end portion of the lower wall 202 is an end portion at which the lower wall 202 is connected to the side wall 203, and the other end portion is an end portion at which the lower wall 202 is connected to the side wall 204.

Figure 7A:
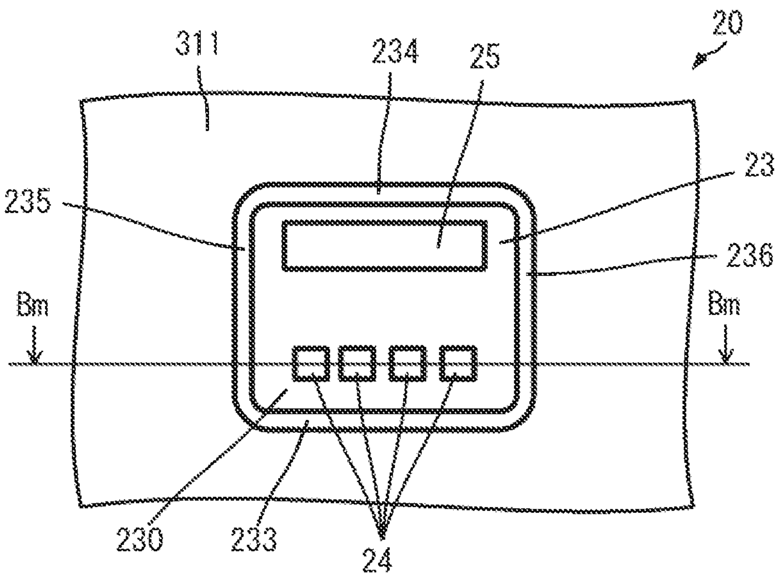
FIG. 7A is an enlarged lower view of a portion including a recess formed on a lower surface of the main unit.
Figure 7B:
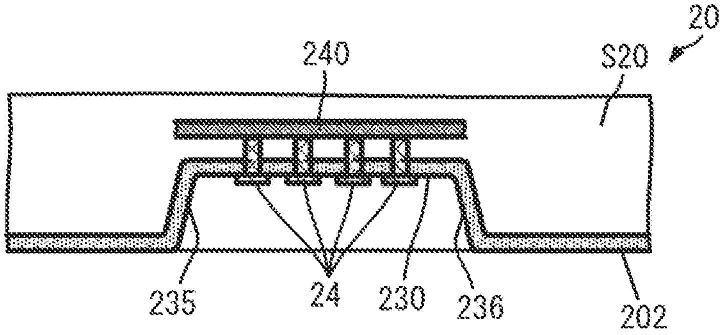
FIG. 7B is an enlarged side sectional view of the portion including the recess formed on the lower surface of the main unit.

FIG. 7A is an enlarged lower view of a portion including a recess formed on a lower surface of the main unit, and FIG. 7B is an enlarged side sectional view of the portion including the recess formed on the lower surface of the main unit. FIG. 7B is a sectional view taken along a line Bm-Bm in FIG. 7A.

The recess 230 has a bottom wall 23, a side wall 233, a side wall 234, a side wall 235, and a side wall 236. The bottom wall 23 is disposed above the lower wall 202 of the housing 200.

The side wall 233, the side wall 234, the side wall 235, and the side wall 236 each connect the bottom wall 23 and the lower wall 202. The side wall 233 connects the bottom wall 23 and a portion of the lower wall 202 on the side wall 203 side, and the side wall 234 connects the bottom wall 23 and a portion of the lower wall 202 on the side wall 204 side. The side wall 235 connects the bottom wall 23 and a portion of the lower wall 202 on the side wall 205 side, and the side wall 236 connects the bottom wall 23 and a portion of the lower wall 202 on a side wall 206 side. A portion constituted of the side wall 233, the side wall 234, the side wall 235, and the side wall 236 corresponds to a "first peripheral portion" of the present disclosure.

A planar area of the bottom wall 23 is smaller than an opening area of the recess 230 at the lower wall 202. Therefore, the side wall 233, the side wall 234, the side wall 235, and the side wall 236 each have an inclined shape in a side view. An angle formed by each of the side wall 233, the side wall 234, the side wall 235, and the side wall 236 and the bottom wall 23 (angle formed inside the recess 230) is larger than 90 degrees.

Multiple connection terminals 24 are disposed on a surface (a surface on a recess 230 side) of the bottom wall 23. The multiple connection terminals 24 are disposed side by side in parallel with the short side direction of the lower wall 202 of the housing 200. A portion of the bottom wall 23 at which the multiple connection terminals 24 are disposed corresponds to a "first electrical connection portion" of the present disclosure, and a portion of the bottom wall 23 around the portion at which the multiple connection terminals 24 are disposed corresponds to a "proximal portion around the first connection terminal" of the present disclosure.

A circuit substrate 240 constituting the first electric circuit is disposed on the bottom wall 23 on an inner space 5200 side. The circuit substrate 240 is connected to the multiple connection terminals 24 with conductors penetrating through the bottom wall 23 in a thickness direction.

A groove 25 is formed in the bottom wall 23. The groove 25 penetrates through the bottom wall 23 and has a shape extending parallel to the short side direction of the lower wall 202.

Base Unit 30

Figure 8:
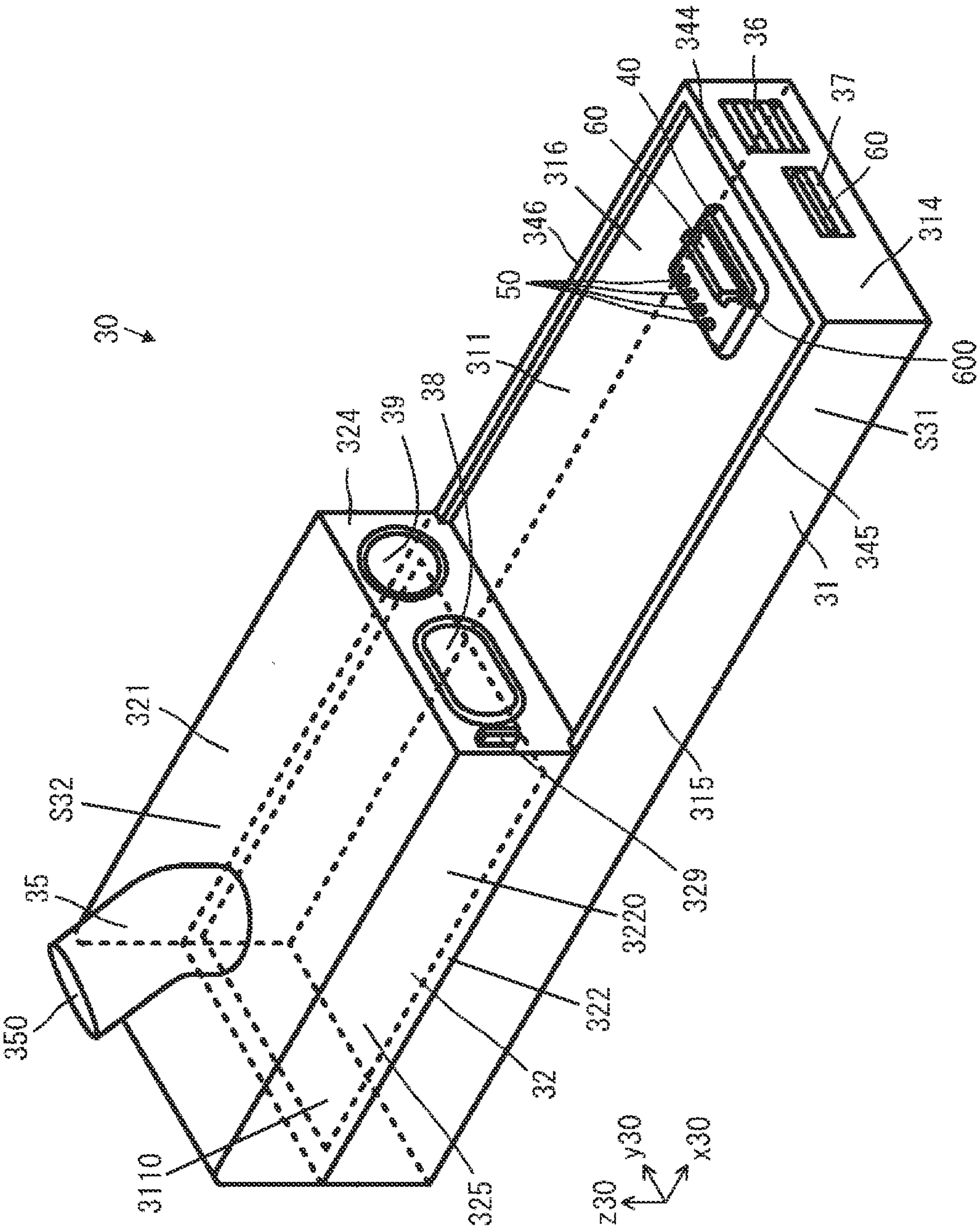
FIG. 8 is an external perspective view of a base unit according to the embodiment of the present disclosure.
Figure 9A:
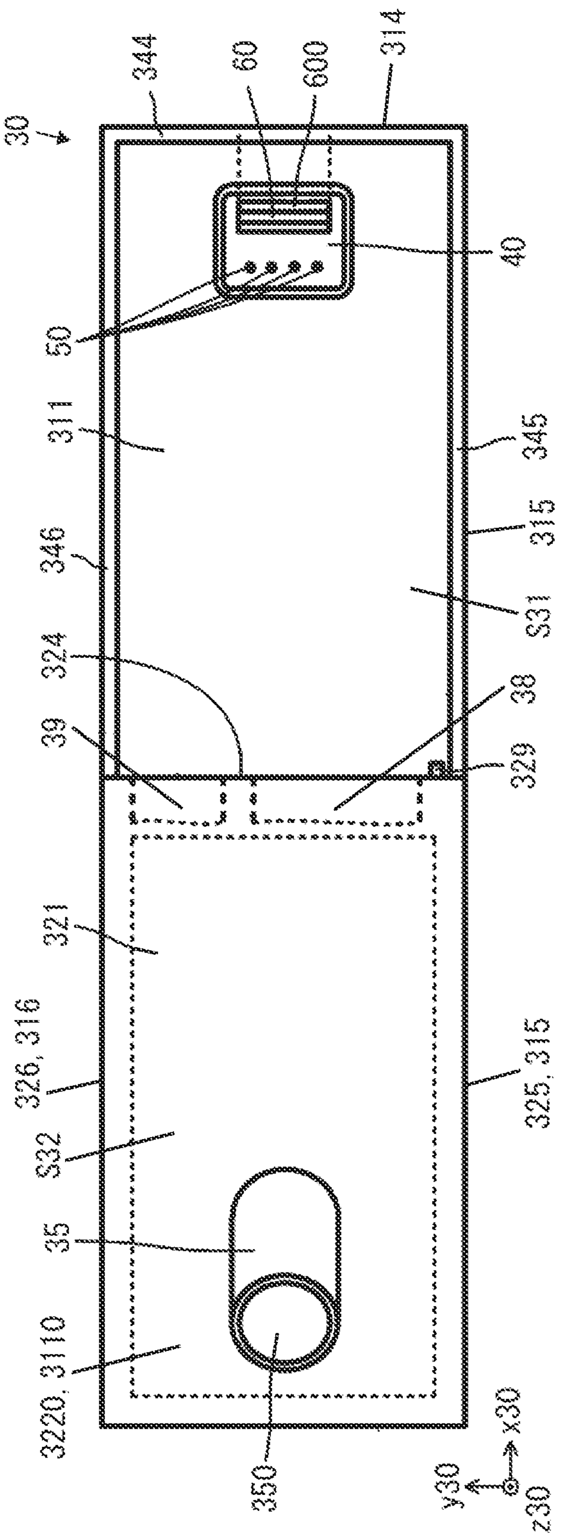
FIG. 9A is a top view of the base unit and FIG. 9B is a side view of the base unit.
Figure 9B:
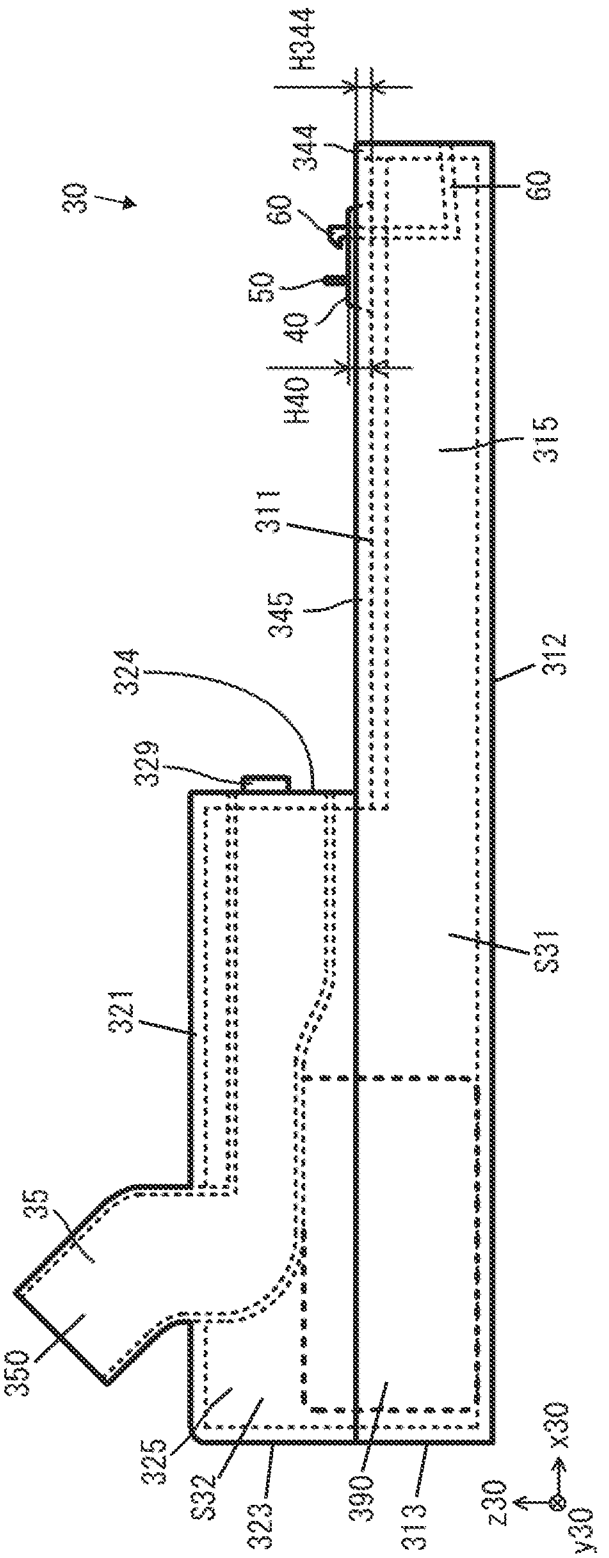
Figure 10A:
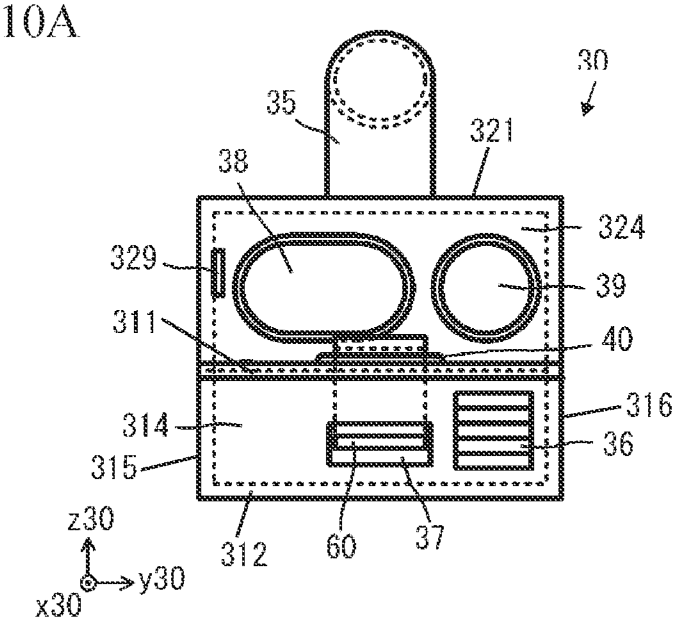
FIG. 10A and FIG. 10B are each a side view of the base unit.
Figure 10B:
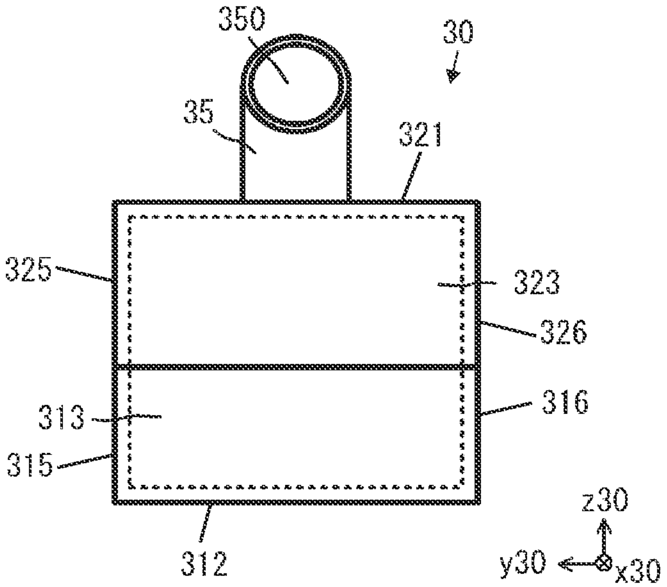

FIG. 8 is an external perspective view of the base unit according to the embodiment of the present disclosure. FIG. 9A is a top view of the base unit, and FIG. 9B, FIG. 10A, and FIG. 10B are each a side view of the base unit. FIG. 9B is a view seen from a long side wall 315 side and a long side wall 325 side, FIG. 10A is a view seen from a short side wall 314 side and a short side wall 324 side, and FIG. 10B is a view seen from a short side wall 313 side and a short side wall 323 side.

The base unit 30 includes multiple housings 31 and 32 as illustrated in FIG. 8, FIG. 9A, FIG. 9B, FIG. 10A, and FIG. 10B.

Base Unit 30 Outline Shape

An outer shape of each of the housing 31 and the housing 32 is a rectangular parallelepiped having a long side direction (x30-axis direction) and a short side direction (y30-axis direction), and having a predetermined height (length in z30-axis direction). A length of the housing 31 in the long side direction is longer than a length of the housing 32 in the long side direction.

The housing 32 is disposed on an upper wall 311 side of the housing 31, and the housing 31 and the housing 32 are connected to each other. The inner space S31 of the housing 31 and the inner space S32 of the housing 32 communicate with each other through an opening 3110 of the housing 31 and an opening 3220 of the housing 32. The housing 32 is rotatable relative to the housing 31 or detachable from the housing 31.

A side wall 313 of the housing 31 and a side wall 323 of the housing 32 are flush with each other, a side wall 315 of the housing 31 and a side wall 325 of the housing 32 are flush with each other, and a side wall 316 of the housing 31 and a side wall 326 of the housing 32 are flush with each other.

Thus, the base unit 30 has a step at an intermediate position in the long side direction, and has a high height portion where the housing 31 and the housing 32 overlap with each other and a low height portion where only the housing 31 is provided.

Housing 31

The housing 31 has an upper wall 311, a lower wall 312, the side wall 313, a side wall 314, the side wall 315, and the side wall 316. The upper wall 311 and the lower wall 312 are opposed to each other. The side wall 313 and the side wall 314 are side walls parallel to the short side direction and are opposed to each other. The side wall 315 and the side wall 316 are side walls parallel to the long side direction and are opposed to each other.

The side wall 313, the side wall 314, the side wall 315, and the side wall 316 are each connected to peripheral portions of the upper wall 311 and the lower wall 312. Thus, the housing 31 has an inner space S31 surrounded by the upper wall 311, the lower wall 312, the side wall 313, the side wall 314, the side wall 315, and the side wall 316. At least part of the second electric circuit is disposed in the inner space S31 (specific illustration is omitted).

The opening 3110 is formed in the upper wall 311. The opening 3110 is a hole penetrating through the upper wall 311 in a thickness direction. The opening 3110 has a predetermined length in the long side direction and is open over substantially the entire upper wall 311 in the short side direction. The opening 3110 is formed so as to leave a predetermined area of the upper wall 311 on a side connected to the side wall 314. In other words, the opening 3110 is formed in a region inside a predetermined width relative to a region in which the housing 32 is disposed.

Frames 344, 345, and 346 are formed on the peripheral portion of the upper wall 311. The frames 344, 345, and 346 protrude upward from an upper surface of the upper wall 311. The frame 344 extends along a connection portion of the upper wall 311 and the side wall 314, the frame 345 extends along a connection portion of the upper wall 311 and the side wall 315, and the frame 346 extends along a connection portion of the upper wall 311 and the side wall 316.

Specific Configuration of Protrusion 40 of Base Unit 30

A protrusion 40 is formed on the upper wall 311. The protrusion 40 has a shape protruding upward (toward the outside of the housing 31) from a surface (corresponding to a "second surface" of the present disclosure) of the upper wall 311. The protrusion 40 is formed at a position closer to the other end portion than to one end portion of the upper wall 311. The one end portion of the upper wall 311 is an end portion at which the upper wall 311 is connected to the step, and the other end portion is an end portion at which the upper wall 311 is connected to the side wall 314.

Figure 11A:
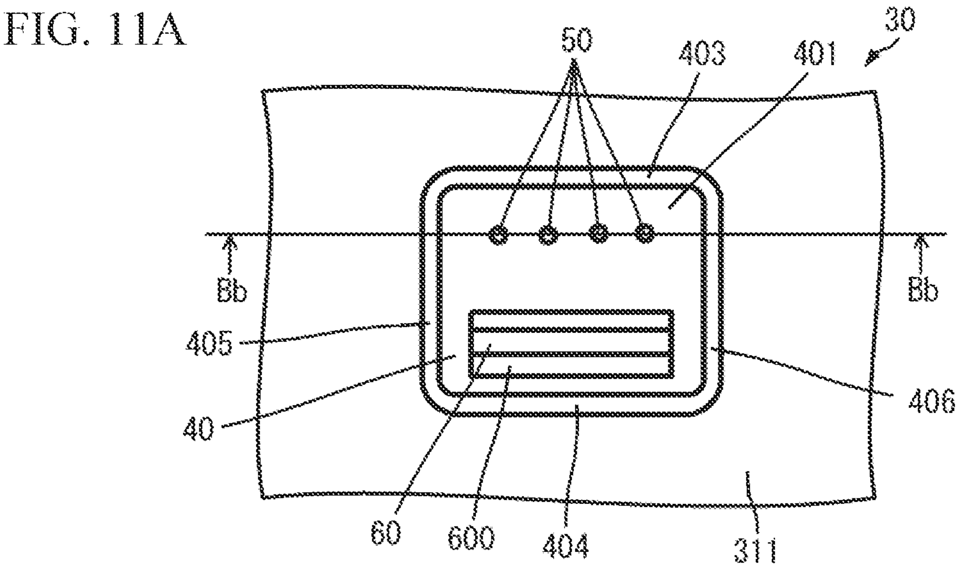
FIG. 11A is an enlarged top view of a portion including a protrusion formed on an upper surface of the base unit.
Figure 11B:
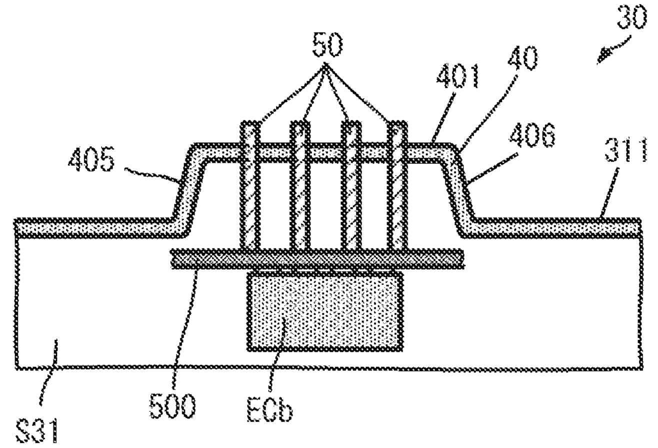
FIG. 11B is an enlarged side sectional view of the portion including the protrusion formed on the upper surface of the base unit.

FIG. 11A is an enlarged upper view of a portion including a protrusion formed on an upper surface of the base unit, and FIG. 11B is an enlarged side sectional view of the portion including the protrusion formed on the upper surface of the base unit. FIG. 11B is a sectional view taken along a line Bb-Bb in FIG. 11A.

The protrusion 40 includes a top wall 401, a side wall 403, a side wall 404, a side wall 405, and a side wall 406. The top wall 401 is disposed above the upper wall 311 of the housing 31.

The side wall 403, the side wall 404, the side wall 405, and the side wall 406 each connect the top wall 401 and the upper wall 311. The side wall 403 connects the top wall 401 and a portion of the upper wall 311 on the side wall 313 side, and the side wall 404 connects the top wall 401 and a portion of the upper wall 311 on the side wall 314 side. The side wall 405 connects the top wall 401 and a portion of the upper wall 311 on the side wall 315 side, and the side wall 406 connects the top wall 401 and a portion of the upper wall 311 on a side wall 316 side. A portion constituted of the side wall 403, the side wall 404, the side wall 405, and the side wall 406 corresponds to a "second peripheral portion" of the present disclosure.

A planar area of the top wall 401 is smaller than a planar area of a portion of the protrusion 40 connected to the upper wall 311. Therefore, the side wall 403, the side wall 404, the side wall 405, and the side wall 406 each have an inclined shape in a side view. An angle formed by each of the side wall 403, the side wall 404, the side wall 405, and the side wall 406 and the top wall 401 (angle formed inside the protrusion 40) is larger than 90 degrees. Further, the angle formed by the top wall 401 and each side wall of the protrusion 40 is substantially the same as the angle formed by the bottom wall 23 and each side wall of the recess 230.

Multiple connection terminals 50 are disposed on a surface of the top wall 401 (exposed surface of the protrusion 40). The multiple connection terminals 50 protrude outward from the surface of the top wall 401 by a predetermined height. The multiple connection terminals 50 are disposed side by side in parallel with the short side direction of the upper wall 311 of the housing 31. A portion of the top wall 401 at which the multiple connection terminals 50 are disposed corresponds to a "second electrical connection portion" of the present disclosure, and a portion of the top wall 401 around the portion at which the multiple connection terminals 50 are disposed corresponds to a "proximal portion around the second connection terminal" of the present disclosure.

A circuit substrate 500 constituting the second electric circuit is disposed in the inner space S31 of the housing 31. An electronic component ECb is mounted on the circuit substrate 500. The circuit substrate 240 is connected to the multiple connection terminals 24 by conductors penetrating through the bottom wall 23 in the thickness direction.

A groove 600 is formed in the top wall 401. A hook member 60 is inserted through the groove 600. The hook member 60 is used when the main unit 20 is attached to and detached from the base unit 30.

CPAP Device 10 Operation Overview

Use of Main Unit 20 Alone

The main unit 20 includes a blower (not illustrated) electrically connected to the first electric circuit. The blower is disposed in the inner space 5200 of the housing 200. When the blower is driven, the main unit 20 sucks air from the inlet 281 and discharges air from the outlet 291. Being provided with the air filter 22 in the inlet 281, the main unit 20 supplies gas (air) having a desired degree of cleanliness to a user from the outlet 291.

Use of Main Unit 20 Attached to Base Unit 30

When the main unit 20 is attached to the base unit 30, the main unit 20 is disposed on an upper surface (upper surface of the upper wall 311) of the low height portion of the base unit 30. The lower wall 202 of the housing 200 of the main unit 20 and the upper wall 311 of the housing 31 of the base unit 30 face each other. At this time, the hook member 60 of the base unit 30 is engaged with the formation portion of the groove 25 of the bottom wall 23 of the recess 230 in the main unit 20, so that the main unit 20 is fixed to the base unit 30.

Further, the outer surface of the side wall 203 of the housing 200 and the outer surface of a side wall 324 of the housing 32 come close to each other or come into contact with each other to be in a close contact state. Note that the side wall 203 and the side wall 324 may be brought into close contact with each other via an elastic body.

At this time, the cylindrical body 290 constituting the outlet 291 of the main unit 20 is inserted into an inlet 39 of the base unit 30. Further, the inlet 281 of the main unit 20 and an outlet 38 of the base unit 30 overlap with each other when viewed from an x-axis (x10-axis). As a result, the flow path forming surface on the side of the main unit 20 and the flow path forming surface on the side of the base unit 30 closely face each other. The inlet 281 of the main unit 20 and the outlet 38 of the base unit 30 are inserted and fitted to each other without causing gas leakage. The outlet 291 of the main unit 20 and the inlet 39 of the base unit 30 are inserted and fitted to each other without causing gas leakage.

When the blower is driven in the state above, the base unit 30 sucks gas from an inlet 36 and discharges the gas from the outlet 38 through the inner space S31 and the inner space S32. The main unit 20 sucks the gas discharged from the outlet 38 through the inlet 281 and discharges the gas from the outlet 291. The base unit 30 sucks the gas discharged from the outlet 291 through the inlet 39 and discharges the gas from an opening 350 of a blower tube 35. Thus, the CPAP device 10 in a state in which the main unit 20 is attached to the base unit 30 supplies gas (air) having a desired degree of cleanliness to a user from the opening 350 of the blower tube 35.

Further, a water storage tank 390 is accommodated in a high height portion of the base unit 30. Furthermore, the base unit 30 is provided with a heater for heating water in the water storage tank.

The base unit 30 has an inlet to take water vapor heated by the heater in a flow path leading from the inlet 39 to the opening 350 of the blower tube 35. In the CPAP device 10 in a state in which the main unit 20 is attached to the base unit 30, water in the water storage tank 390 is heated by the heater to vaporize, and gas (air) having a desired humidity is supplied to a user from the opening 350 of the blower tube 35.

Specific Configuration of Electrical Connection Portion

Figure 12A:
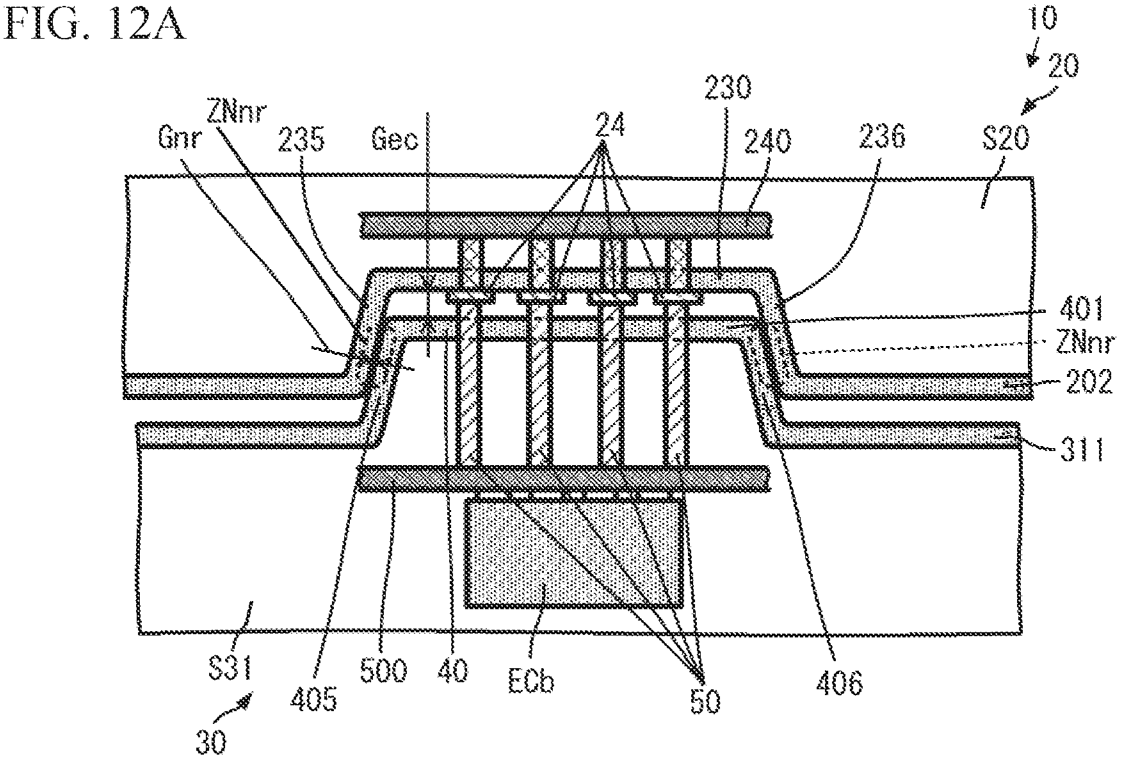
FIG. 12A is an enlarged side sectional view of an electrical connection portion between the main unit and the base unit.
Figure 12B:
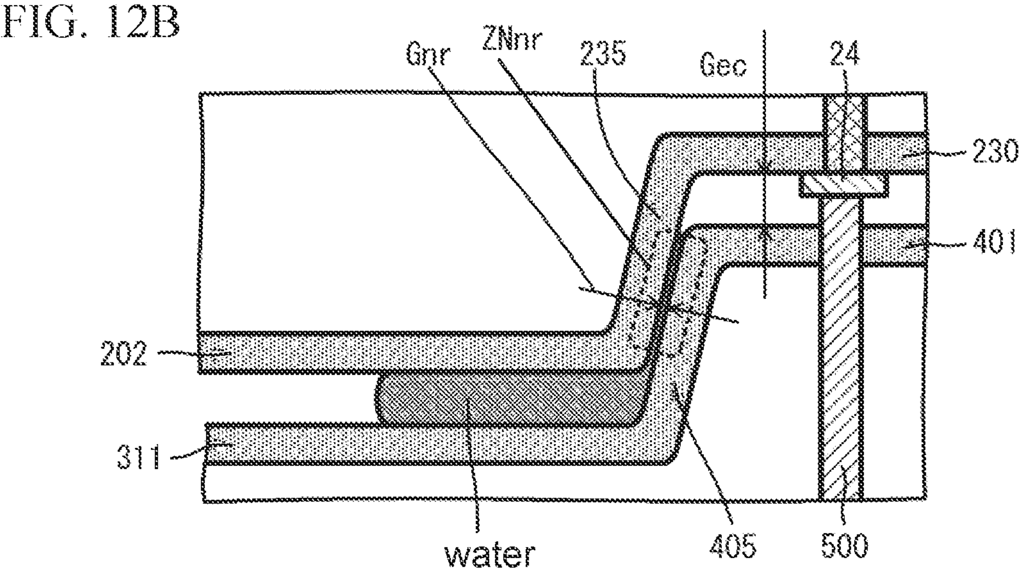
FIG. 12B is a view illustrating a concept to suppress the entry of water.

FIG. 12A is an enlarged side sectional view of an electrical connection portion between the main unit and the base unit, and FIG. 12B is a view illustrating a concept to suppress the entry of water.

The protrusion 40 of the base unit 30 is inserted into the recess 230 of the main unit 20 as illustrated in FIG. 12A and FIG. 12B. The multiple connection terminals 50 of the base unit 30 are each brought into contact with and electrically connected to each of the multiple connection terminals 24 of the main unit 20.

At this time, the multiple connection terminals 50 are pushed in by the main unit 20 (multiple connection terminals 24). With this, the multiple connection terminals 50 generate the biasing force in a direction (electrical connection direction) to connect to the multiple connection terminals 24. As a result, the connection resistance between the multiple connection terminals 50 and the multiple connection terminals 24 may be lowered, and the reliability of electrical connection is increased.

In the state above, the top wall 401 of the protrusion 40 and the bottom wall 23 of the recess 230 face each other. Further, the side wall 403 of the protrusion 40 faces the side wall 233 of the recess 230. The side wall 404 of the protrusion 40 faces the side wall 234 of the recess 230. The side wall 405 of the protrusion 40 faces the side wall 235 of the recess 230. The side wall 406 of the protrusion 40 faces the side wall 236 of the recess 230.

A distance between surfaces of the top wall 401 and the bottom wall 23 facing each other (distance between the first electrical connection portion and the second electrical connection portion facing each other) is Gec (hereinafter referred to as a spatial distance Gec). More specifically, the spatial distance Gec is a distance between the surface of the top wall 401 on a bottom wall 23 side being a surface of a proximal portion around the multiple connection terminals 50, and a surface of the bottom wall 23 on a top wall 401 side being a surface of a proximal portion around the multiple connection terminals 24. That is, the spatial distance Gec is a spatial distance between the proximal portions of the connection terminals. When the spatial distance Gec varies in a region where the top wall 401 and the bottom wall 23 face each other, the minimum value is the spatial distance Gec. The spatial distance Gec corresponds to a "second distance" of the present disclosure.

A distance between surfaces of the side wall 405 and the side wall 235 facing each other (distance between the first peripheral portion and the second peripheral portion facing each other) is Gnr (hereinafter, referred to as a spatial distance Gnr of the peripheral portion). More specifically, the spatial distance Gnr of the peripheral portion is a distance between a surface of the side wall 405 on a side wall 235 side and a surface of the side wall 235 on a side wall 405 side. In a case that the spatial distance Gnr of the peripheral portion has variation in a region where the side wall 405 and the side wall 235 face each other, the maximum value is the spatial distance Gnr of the peripheral portion. The spatial distance Gnr corresponds to a "first distance" of the present disclosure.

Similarly, the side wall 403 and the side wall 233 face each other with the spatial distance Gnr of the peripheral portion, the side wall 404 and the side wall 234 face each other with the spatial distance Gnr of the peripheral portion, and the side wall 406 and the side wall 236 face each other with the spatial distance Gnr of the peripheral portion. In the case above, when the spatial distance Gnr between the side wall 403 and the side wall 233, the spatial distance Gnr between the side wall 404 and the side wall 234, the spatial distance Gnr between the side wall 405 and the side wall 235, and the spatial distance Gnr between the side wall 406 and the side wall 236 are different from each other, the maximum value is the spatial distance Gnr of the peripheral portion.

The spatial distance Gnr of the peripheral portion is shorter than the spatial distance Gec of the proximal portion of the connection terminals as illustrated in FIG. 12A and FIG. 12B. The spatial distance Gnr of the peripheral portion is preferably 0.7 mm or less, and in particular, approximately 0.15 mm, for example. On the other hand, the spatial distance Gec of the proximal portion of the connection terminals is 0.8 mm or more.

In the configuration described above, when the main unit 20 is attached to the base unit 30 with water being present between the upper wall 311 of the base unit 30 and the lower wall 202 of the main unit 20 (outside the portion where the recess 230 and the protrusion 40 face each other), the water reaches the portion where the side wall 405 and the side wall 235 face each other (a narrow region ZNnr in the peripheral portion) as illustrated in FIG. 12B, but does not reach the proximal portion of the connection terminals where the top wall 401 and the bottom wall 23 face each other.

The phenomenon above occurs because of a capillary phenomenon caused by the fact that the spatial distance Gnr of the peripheral portion (narrow region ZNnr) is shorter than the spatial distance Gec of the proximal portion of the connection terminals. In particular, as described above, with the spatial distance Gnr of the peripheral portion being approximately 0.15 mm or less, the capillary phenomenon may more reliably be generated.

Therefore, in the CPAP device 10, even when water is present on the surface of the upper wall 311 of the base unit 30, the entry of water into the proximal portion of the connection terminals may be prevented. As a result, the CPAP device 10 may suppress undesired short circuit of the multiple connection terminals 24 and undesired short circuit of the multiple connection terminals 50. In particular, as described above, with the spatial distance Gnr of the peripheral portion being approximately 0.15 mm or less, it is possible to more reliably suppress the retention of water in the peripheral portion because of a capillary phenomenon and the entry of water into the proximal portion of the connection terminals.

Note that the spatial distance Gnr of the peripheral portion is not limited to the above-described specific example. It is sufficient that the spatial distance Gnr of the peripheral portion (narrow region ZNnr) is set to be shorter than the spatial distance Gec of the proximal portion of the connection terminals, and is set based on a liquid such as water handled by the CPAP device 10 and a close contact degree of each side wall of the protrusion 40 and the recess 230 so that the capillary phenomenon occurs.

Further, in the above-described configuration, illustrated is the case that the narrow region ZNnr is provided on an entire circumference surrounding the proximal portion of the connection terminals in plan view. However, even in a configuration in which the narrow region ZNnr is partially missing, the effect of suppressing the entry of water into the proximal portion of the connection terminals may be obtained as compared with a configuration in which the narrow region ZNnr does not exist at all. Further, in a region where the narrow region ZNnr is missing, an elastic dam material or the like may be disposed so as to be sandwiched between the upper wall 311 and the lower wall 202.

Further, in the CPAP device 10, the height of the frames 344, 345, and 346 of the base unit 30 is made higher than a height of the protrusion 40. In other words, the height of the protrusion 40 is greater than the height of the frames 344, 345, and 346 of the base unit 30. With this, in the CPAP device 10, even when water is present on the upper wall 311 up to the height of the frames 344, 345, and 345, the entry of water into the proximal portion of the connection terminals may be suppressed.

Modification 1

Figure 13:
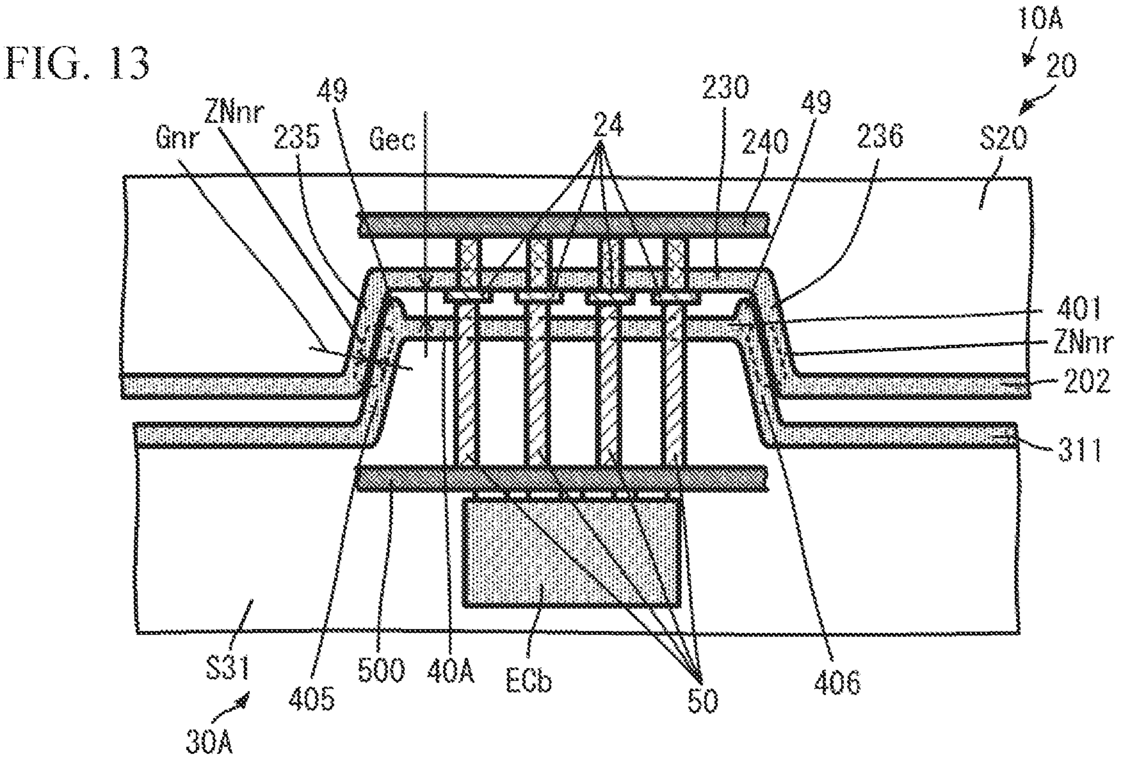
FIG. 13 is an enlarged side sectional view of an electrical connection portion between a main unit and a base unit according to Modification 1.

FIG. 13 is an enlarged side sectional view of an electrical connection portion between a main unit and a base unit according to Modification 1.

A CPAP device 10A of Modification 1 is different from the above-described CPAP device 10 in the shape of a protrusion 40A of a base unit 30A. Other configurations of the CPAP device 10A are the same as those of the CPAP device 10, and a description of the same portions is omitted.

The protrusion 40A includes a frame 49 protruding upward from the surface of the top wall 401 on a peripheral portion of the top wall 401.

With the configuration above, the CPAP device 10A may further suppress the entry of water into the proximal portion of the connection terminals.

Modification 2

Figure 14:
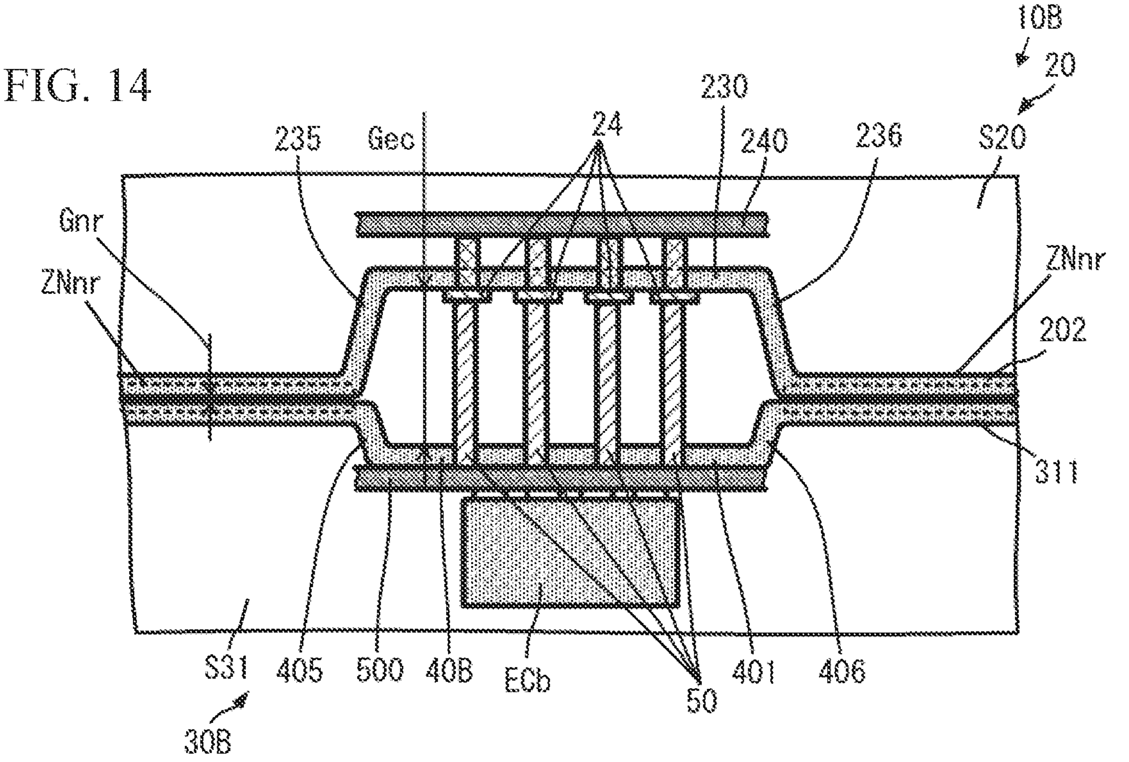
FIG. 14 is an enlarged side sectional view of an electrical connection portion between a main unit and a base unit according to Modification 2.

FIG. 14 is an enlarged side sectional view of an electrical connection portion between a main unit and a base unit according to Modification 2.

A CPAP device 10B of Modification 2 is different from the above-described CPAP device 10 in that a base unit 30B has a recess 40B. Other configurations of the CPAP device 10B are the same as those of the CPAP device 10, and a description of the same portions is omitted.

The base unit 30B has the recess 40B. The recess 40B is obtained by forming the above-described protrusion 40 on an inner space S31 side of the housing 31. In other words, the recess 40B has a shape protruding toward the inner space S31 side of the housing 31.

The CPAP device 10B forms a narrow region ZNnr in the peripheral portion with a portion in which the lower wall 202 of the main unit 20 and the upper wall 311 of the base unit 30B face each other.

With the configuration described above, the CPAP device 10B may achieve the same operational effects as the CPAP device 10 does.

<1> A CPAP device, comprising: a main unit including a first electric circuit including a blower and a first connection terminal connected to the first electric circuit; and a base unit connectable to the main unit, including a blower tube, a second electric circuit, and a second connection terminal connected to the second electric circuit, wherein the main unit includes a first electrical connection portion including an exposed portion of the first connection terminal and a first peripheral portion surrounding the first electrical connection portion, the base unit includes a second electrical connection portion including an exposed portion of the second connection terminal and a second peripheral portion surrounding the second electrical connection portion, and a first distance with which the first peripheral portion and the second peripheral portion face each other has a portion shorter than a second distance with which a proximal portion of the first electrical connection portion around the first connection terminal and a proximal portion of the second electrical connection portion around the second connection terminal face each other.

<2> The CPAP device according to <1>, wherein over an entire periphery of a portion where the proximal portion of the first electrical connection portion around the first connection terminal and the proximal portion of the second electrical connection portion around the second connection terminal face each other, the first distance is shorter than the second distance.

<3> The CPAP device according to <1> or <2>, wherein the main unit has a first surface, and the first electrical connection portion is disposed on a bottom surface of a recess recessed from the first surface, the base unit has a second surface, and the second electrical connection portion is disposed on a top surface of a protrusion protruding from the second surface, and the first peripheral portion is a side surface of the recess, and the second peripheral portion is a side surface of the protrusion.

<4> The CPAP device according to <3>, wherein the base unit has a first frame higher than the protrusion outside the second peripheral portion on the second surface.

<5> The CPAP device according to <3> or <4>, wherein the second electrical connection portion includes a second frame surrounding the second connection terminal when viewed from a direction orthogonal to the second surface.

<6> The CPAP device according to any one of <1> to <5>, wherein the first distance is 0.15 mm.

<7> The CPAP device according to any one of <1> to <6>, wherein the base unit includes a storage tank configured to store water.

What is claimed is:

1. A continuous positive airway pressure (CPAP) device, comprising:

a main unit including a first electric circuit including a first connection terminal connected to the first electric circuit; and a base unit connectable to the main unit, including a blower tube, a second electric circuit, and a second connection terminal connected to the second electric circuit, wherein the main unit includes a first electrical connection portion including an exposed portion of the first connection terminal and a first peripheral portion surrounding the first electrical connection portion, the base unit includes a second electrical connection portion including an exposed portion of the second connection terminal and a second peripheral portion surrounding the second electrical connection portion, a first distance with which the first peripheral portion and the second peripheral portion face each other has a portion shorter than a second distance with which a proximal portion of the first electrical connection portion around the first connection terminal and a proximal portion of the second electrical connection portion around the second connection terminal face each other, wherein the main unit has a first surface, and the first electrical connection portion is disposed on a bottom surface of a recess along a recessing direction into the first surface, wherein the first peripheral portion is a side surface of the recess connecting the bottom surface with the first surface, wherein the base unit has a second surface and the second electrical connection portion is disposed on a top surface of a protrusion along a protruding direction from the second surface, and wherein a side wall of the protrusion connects the top surface of the protrusion to the second surface.

2. The CPAP device according to claim 1, wherein over an entire periphery of a portion where the proximal portion of the first electrical connection portion around the first connection terminal and the proximal portion of the second electrical connection portion around the second connection terminal face each other, the first distance is shorter than the second distance.

3. The CPAP device according to claim 1, wherein the base unit has a frame higher than the protrusion outside the second peripheral portion on the second surface.

4. The CPAP device according to claim 1, wherein the second electrical connection portion includes a frame surrounding the second connection terminal when viewed from a direction orthogonal to the second surface.

5. The CPAP device according to claim 1, wherein the first distance is 0.15 mm.

6. The CPAP device according to claim 1, wherein the base unit includes a storage tank configured to store water.

7. The CPAP device according to claim 2, wherein the first distance is 0.15 mm.

8. The CPAP device according to claim 2, wherein the base unit includes a storage tank configured to store water.

* * * * *